United States Patent [19]
Kemsley

[11] Patent Number: 5,440,126
[45] Date of Patent: Aug. 8, 1995

[54] OPTICAL PROBE HEADS

[75] Inventor: Evelyn E. K. Kemsley, Norwich, England

[73] Assignee: British Technology Group Ltd., London, England

[21] Appl. No.: 140,013

[22] PCT Filed: Apr. 23, 1992

[86] PCT No.: PCT/GB92/00744
§ 371 Date: Oct. 25, 1993
§ 102(e) Date: Oct. 25, 1993

[87] PCT Pub. No.: WO92/19956
PCT Pub. Date: Nov. 12, 1992

[30] Foreign Application Priority Data
Apr. 26, 1991 [GB] United Kingdom ............... 9108974

[51] Int. Cl.6 .................. G01N 21/55; G01N 21/31
[52] U.S. Cl. ................. 250/339.12; 250/341.2; 356/300
[58] Field of Search ............ 250/343, 341, 339.01, 250/339.06, 339.12, 341.2, 341.8, 339.11, 339.07; 356/244, 300, 133, 136

[56] References Cited
U.S. PATENT DOCUMENTS

| 3,591,287 | 7/1971 | Rodsey . | |
|---|---|---|---|
| 3,669,545 | 6/1972 | Gilby . | |
| 3,751,672 | 8/1973 | Michel et al. | 356/136 |
| 4,595,833 | 6/1986 | Sting . | |
| 4,602,869 | 7/1986 | Harrick | 356/244 |

FOREIGN PATENT DOCUMENTS

| 678820 | 9/1966 | Belgium . | |
|---|---|---|---|
| 0209489 | 1/1987 | European Pat. Off. . | |
| 0221011 | 6/1987 | European Pat. Off. . | |
| 1772690 | 5/1971 | Germany . | |
| 0019745 | 1/1990 | Japan | 356/133 |
| 674082 | 4/1990 | Switzerland . | |
| 1032565 | 6/1966 | United Kingdom . | |
| 2186387 | 8/1987 | United Kingdom . | |

Primary Examiner—Constantine Hannaher
Assistant Examiner—Edward J. Glick
Attorney, Agent, or Firm—Cushman, Darby & Cushman

[57] ABSTRACT

Apparatus for use in optical spectroscopy comprises an input fiber (21) for launching by way of a collimating lens (22) radiation towards a chamfered input surface (23) of a probe head (24) of sapphire and having at least five surfaces (25-29) exposable to a sample under test and a chamfered exit surface 30 positioned to direct the radiation towards a further lens (31) and an output fiber (32).

13 Claims, 2 Drawing Sheets

OPTICAL PROBE HEADS

BACKGROUND OF THE INVENTION

1. Field of the Invention

This invention relates to probe heads and, in particular, to probe heads utilizing the mechanism of attenuated total reflectance for use in infra-red spectroscopy.

2. Description of Related Art

Attenuated total Reflectance (ATR) crystals use the total internal reflectance to effect an interaction between a sample and beams of radiation of wavelengths suitable for infra-red spectroscopy.

Total internal reflection occurs when the crystal material is optically denser (i.e. has a greater refractive index) than the surrounding medium, provided that the angle of incidence $\alpha_1$ fulfills a certain condition.

BRIEF DESCRIPTION OF THE DRAWINGS

The invention will now be particularly described with reference to the accompanying drawings, in which.

DESCRIPTION OF PREFERRED EMBODIMENTS

Figure 1:
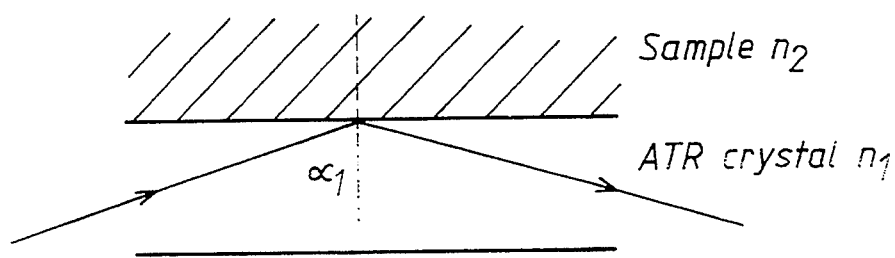
FIG. 1 is an explanatory diagram.

FIG. 1 is an explanatory diagram which shows radiation incident at an angle $\alpha_1$ on an interface between an attenuated total reflectance crystal of refractive index $n_1$ and a sample of refractive index $n_2$. The penetration of the evanescent wave at an interface is given by $$d = \frac{\lambda}{2\pi[\sin^2\alpha_1 - (n_2/n_1)^2]^{\frac{1}{2}}}$$

provided that $\sin\alpha_1 > n_2/n_1$. If $\sin\alpha_1 \leq n_2/n_1$, then total internal reflection does not take place. Instead the ray is transmitted out of the crystal in accordance with Snell's law ($n_1 \sin\alpha_1 = n_2 \sin\alpha_2$).

Typical samples may have indices in the region 1.3-1.5. For these, the minimum interface angle which will produce an acceptable penetration depth is dependent on the material used for the ATR crystal. Conventionally, high refractive index substances are used, such as zinc selenide, zinc sulphide, silicon or germanium. However, the mechanical and toxic qualities of these materials make them unsuitable for use in probe heads.

Figure 2:
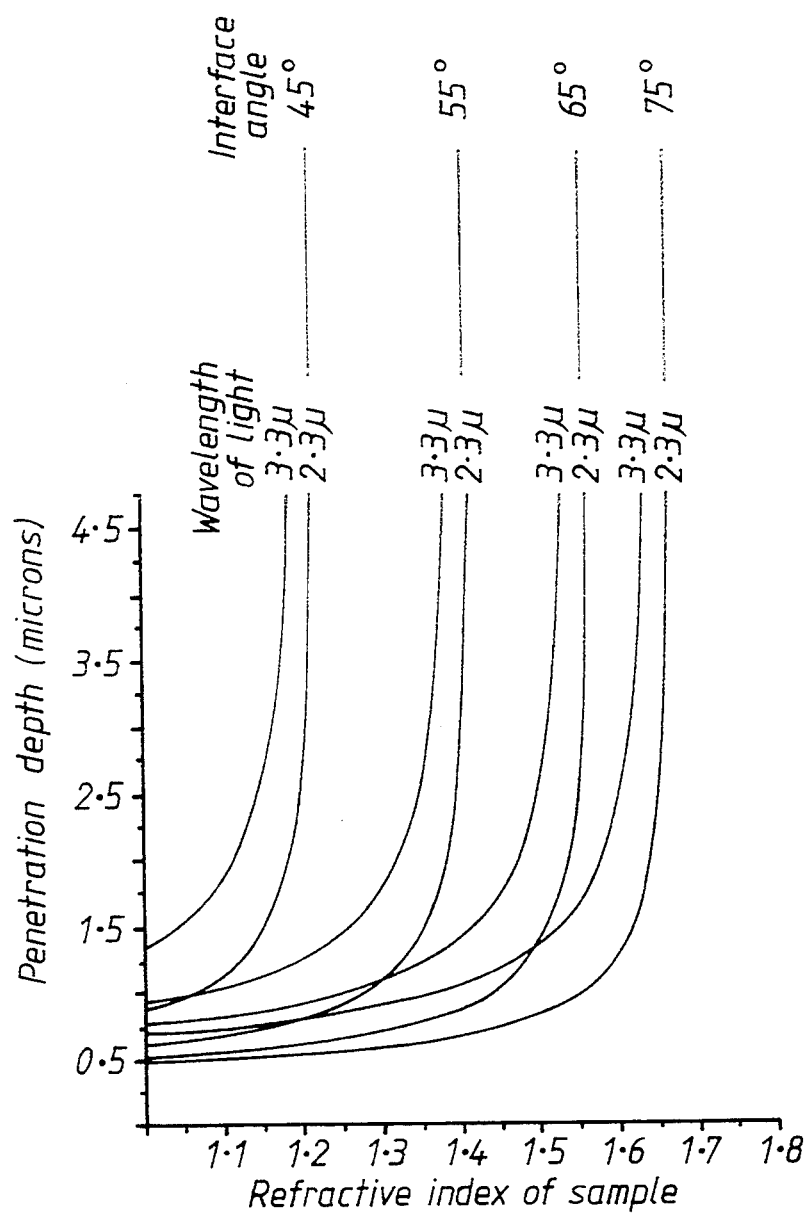
FIG. 2 is a series of graphs showing the variation of penetration depth with incident angle, refractive index and wavelength.

Referring now to FIG. 2 of the drawings, a wide variety of different graphs can be constructed showing the variation of penetration depth with wavelength, angle, refractive indices etc. The series of plots shows the penetration depths obtained in sapphire against the refractive index of a sample under test for different values of $\alpha_1$, $n_1$ and $\lambda$.

Sapphire possesses superior mechanical properties and is non-toxic. However, the minimum interface angle which will produce an acceptable penetration depth is 65°. Below this angle, only samples with very low indices will exhibit total internal reflection.

For angles 65° and above total internal reflection may occur. The penetration depth, however, is such that several reflections (at least 4) are necessary to produce overall pathlengths large enough for good quality spectra.

Due to these requirements, traditional ATR crystal shapes are not suitable for sapphire.

The internal angles of an octagon are 135°. If a light ray is reflected internally between faces, this corresponds to $\alpha_1 = 67.5°$. Thus suitable sapphire ATR crystals may be based on the geometry of an octagon.

A four-reflection crystal would accommodate parallel input and output beams. However, these will necessarily be very close to the sides of the crystal, making the mounting of both the launching optics and the crystal itself very difficult unless a very large crystal is used. We have found that this problem may be overcome by using a five-reflection crystal, desirably, with chamfered input and output faces.

According to the present invention there is provided a probe head for use in attenuated total reflectance optical spectroscopy incorporating a prism having surfaces adapted to provide at least five interfaces with a sample of a material under test at which substantially total internal reflection of a beam of radiation may take place successively.

Figure 3:
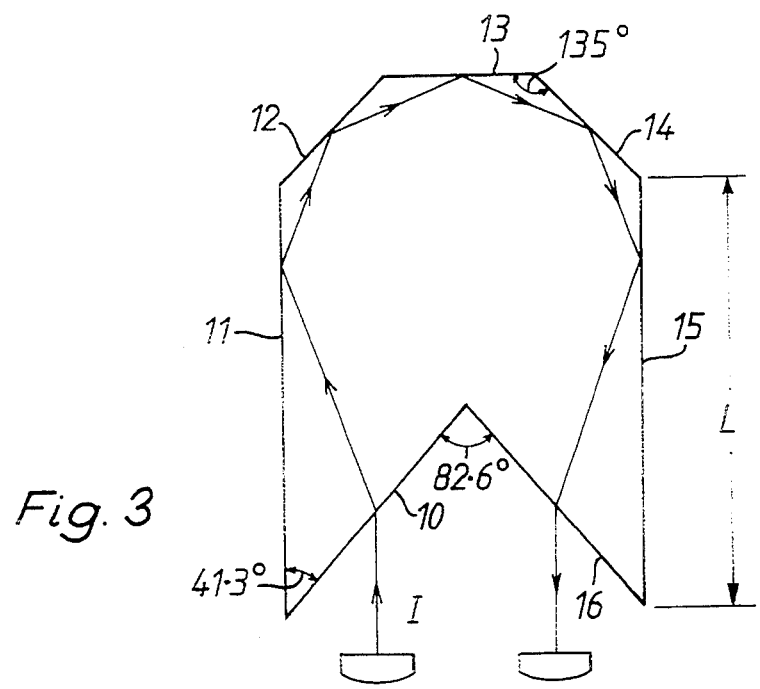
FIG. 3 is a diagrammatic representation of a section through an ATR head in accordance with a specific embodiment of the invention.

FIG. 3 shows diagrammatically the path followed by an incident beam of radiation I which is refracted at an input face 10 and totally internally reflected at five probe head-sample interfaces 11-15 before being refracted at an output surface 16.

If the input and output face angles are suitably determined, the input and output rays can be deflected to be parallel.

By controlling the distance L between the first reflection and the chamfered faces, the relative displacement of the exit beam and the entrance beams is controlled.

Five reflections are sufficient to give an acceptable total path length in the region 1-5 $\mu$m of the infra-red.

Figure 4:
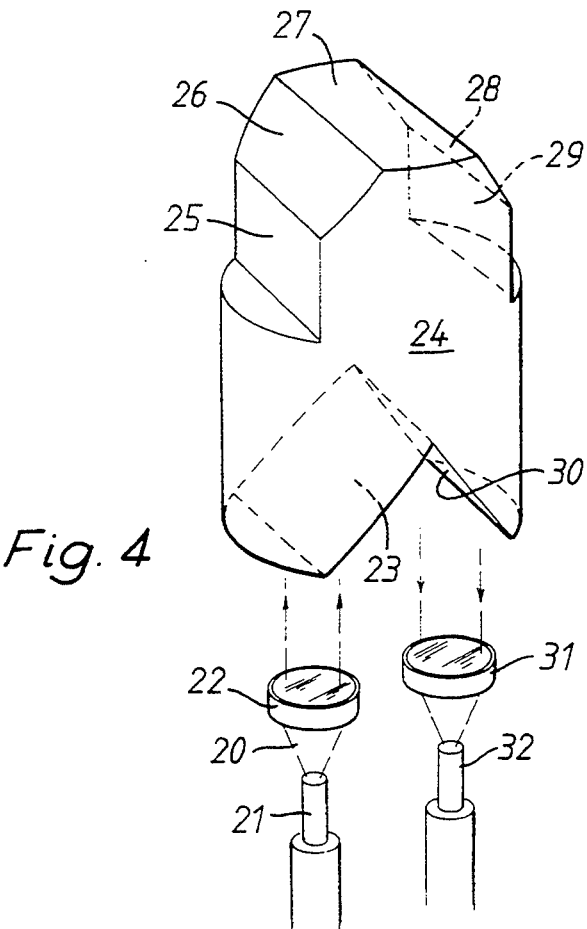
FIG. 4 shows one form of apparatus envisaged by the invention.

FIG. 4 is an isometric view of a practical embodiment of the apparatus. Radiation 20 from an input optical fiber 21 passes by way of a collimating lens 22 to the input face 23 of a probe head 24. Reflections take place internally at surfaces 25-29, after which the beam passes by way of exit surface 30 to a further lens 31 and output fiber 32.

The chamfered faces allow the dimensions of the crystal to be minimized and matched to the size of the coupling optics. Furthermore, the reflecting faces can be cut into a basic cylinder shaped crystal, facilitating airtight mounting and sealing of the crystal.

I claim:

1. A probe head for use in attenuated total reflectance optical spectroscopy including a prism, said prism comprising:
   a chamfered input face for accepting a beam of radiation as an input beam of radiation into said prism;
   a plurality of reflecting surfaces each providing an interface between said prism and a sample of a material under test, said input beam of radiation being substantially totally reflected internal to said prism in succession by said plurality of reflecting surfaces; and
   a chamfered output face for releasing said input beam of radiation external to said prism as an output beam of radiation substantially parallel to said beam of radiation accepted by said chamfered input face.

2. A probe head for use in attenuated total reflectance optical spectroscopy according to claim 1, wherein said prism has five reflecting surfaces.

3. A probe head for use in attenuated total reflectance optical spectroscopy according to claim 1, wherein said plurality of reflecting faces of said prism form a substantially cylindrically-shaped crystal.

4. A probe head for use in attenuated total reflectance optical spectroscopy according to any one of claims 1 to 3, wherein a material of said prism is sapphire.

5. A probe head for use in attenuated total reflectance optical spectroscopy according to claim 1, wherein an angle internal to said prism between a first one of said plurality of reflecting surfaces and said chamfered input face is less than 90 degrees.

6. A probe head for use in attenuated total reflectance optical spectroscopy according to claim 1, wherein an angle internal to said prism between a last one of said plurality of reflecting surfaces and said chamfered output face is less than 90 degrees.

7. A probe head for use in attenuated total reflectance optical spectroscopy according to claim 1, wherein an angle internal to said prism between any two of said plurality of reflecting surfaces is greater than 90 degrees.

8. A probe head for use in attenuated total reflectance optical spectroscopy according to claim 1, wherein an angle internal to said prism between said chamfered input face and said chamfered output face is about 82.6 degrees.

9. A probe apparatus for use in attenuated total reflectance optical spectroscopy comprising:
   an input fiber for launching radiation;
   a input collimating lens receiving said radiation launched from said input fiber and producing a beam of radiation;
   a prism comprising:
     a chamfered input face for accepting said beam of radiation produced by said collimating lens as an input beam of radiation into said prism,
     a plurality of reflecting surfaces each providing an interface between said prism and a sample of a material under test, said input beam of radiation being substantially totally reflected internal to said prism in succession by said plurality of reflecting surfaces, and
     a chamfered output face for releasing said input beam of radiation external to said prism as an output beam of radiation substantially parallel to said beam of radiation accepted by said chamfered input face;
   a further lens receiving said radiation released by said chamfered output face of said prism and producing a beam of radiation; and
   an output fiber accepting said beam of radiation produced by said further lens.

10. A probe apparatus for use in attenuated total reflectance optical spectroscopy according to claim 9, wherein an angle internal to said prism between a first one of said plurality of reflecting surfaces and said chamfered input face is less than 90 degrees.

11. A probe apparatus for use in attenuated total reflectance optical spectroscopy according to claim 9, wherein an angle internal to said prism between a last one of said plurality of reflecting surfaces and said chamfered output face is less than 90 degrees.

12. A probe apparatus for use in attenuated total reflectance optical spectroscopy according to claim 9, wherein an angle internal to said prism between any two of said plurality of reflecting surfaces is greater than 90 degrees.

13. A probe head for use in attenuated total reflectance optical spectroscopy according to claim 9, wherein an angle internal to said prism between said chamfered input face and said chamfered output face is about 82.6 degrees.

* * * * *